Figure 1:
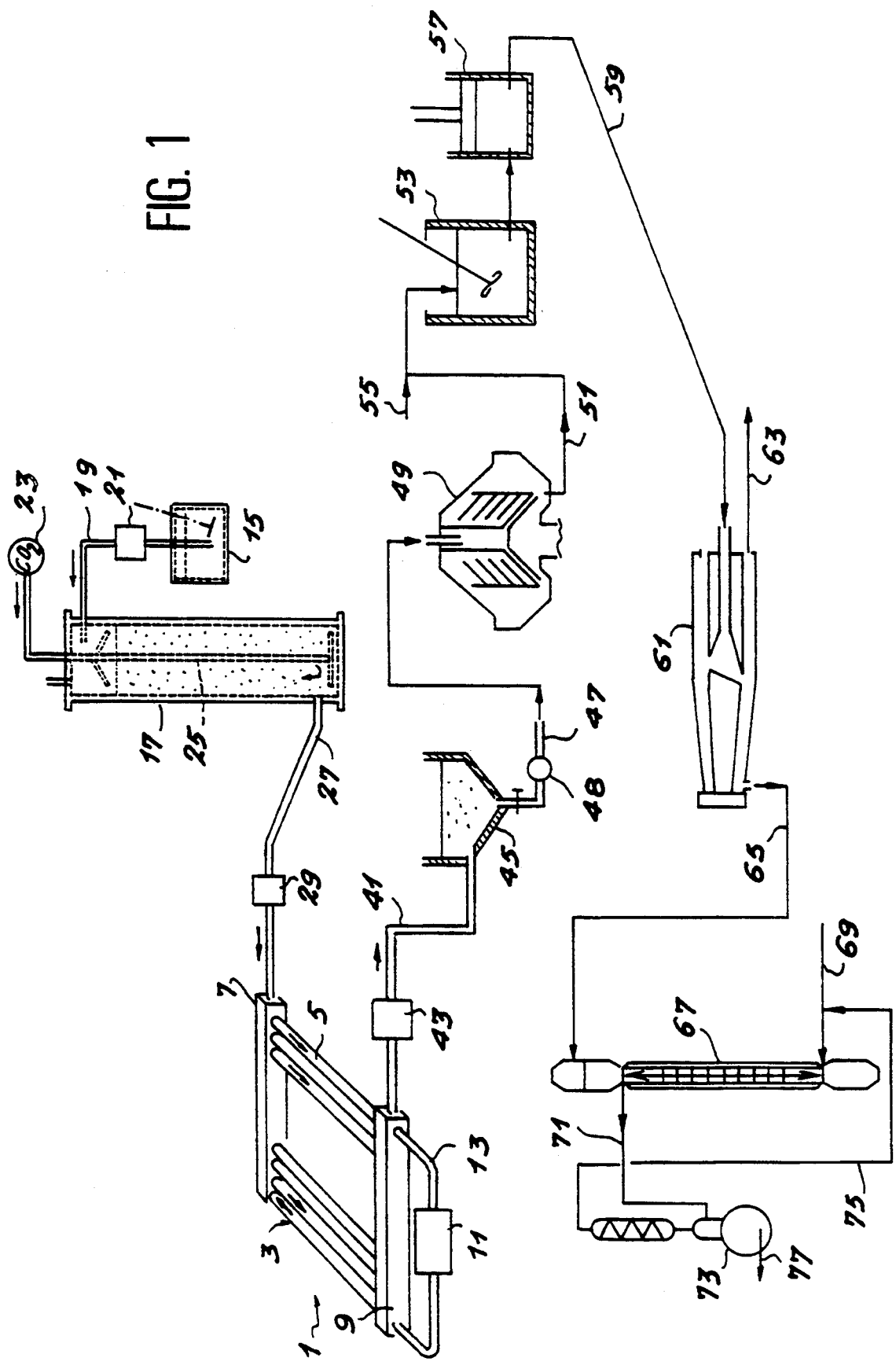

United States Patent [19]

Thepenier et al.

[11] Patent Number: 5,338,673
[45] Date of Patent: Aug. 16, 1994

[54] PROCESS FOR THE SELECTIVE PRODUCTION OF POLYUNSATURATED FATTY ACIDS FROM A CULTURE OF MICROALGAE OF THE PORPHYRIDIUM CRUENTUM

[75] Inventors: Catherine Thepenier, Manosque; Claude Gudin, Aix en Provence; Bruno Sarrobert, Manosque, all of France

[73] Assignees: Commissariat a L'Energie Atomique, Paris; Societe USSI, Saint Quentin Yvelines Cedex, both of France

[21] Appl. No.: 8,710

[22] Filed: Jan. 25, 1993

[30] Foreign Application Priority Data

Jan. 28, 1992 [FR] France ............... 92 00861

[51] Int. Cl.$^5$ ............... C12P 7/64; A01H 13/00
[52] U.S. Cl. ............... 435/134; 435/257.1; 435/946; 47/1.4
[58] Field of Search ............... 47/1.4; 435/134, 946, 435/257.1

[56] References Cited

U.S. PATENT DOCUMENTS

| | | | |
|---|---|---|---|
| 3,986,297 | 10/1976 | Ichimura et al. | 47/1.4 |
| 4,417,415 | 11/1983 | Cysewski et al. | 47/1.4 |
| 4,721,584 | 1/1988 | Arai et al. | 47/1.4 |

OTHER PUBLICATIONS

Journal of Phycology, vol. 24, No. 3, Sep. 1988, pp. 328–332, Zvi Cohen, et al., "Effect of Environmental Conditions on Fatty Acid Composition of the Red Alga Porphyridium Cruentum: Correlation to Growth Rate".

Mircen Journal of Applied Microbiology and Biotechnology, vol. 4, No. 2, 1988, pp. 231–237, Y. K. Lee, et al., "Effect of Temperature, Light Intensity and Dilution Rate on the Cellular Composition of Red Alga Porphyridium Cruentum in Light Limited Chemostat Cultures".

*Primary Examiner*—Douglas W. Robinson
*Assistant Examiner*—Maria Luisa Osoteo
*Attorney, Agent, or Firm*—Oblon, Spivak, McClelland, Maier & Neustadt

[57] ABSTRACT

The invention relates to a process for the selective production of polyunsaturated fatty acids from a culture of microalgae of *Porphyrium cruentum*. The process comprises growing a biomass by culturing the microalgae in a photobioreactor under optimum culturing conditions, removing a portion of the resulting biomass, and subjecting the removed portion to a temperature decrease. The result is the selective increase in the quantity of a given polyunsaturated fatty acid within the microalgae biomass.

9 Claims, 3 Drawing Sheets

PROCESS FOR THE SELECTIVE PRODUCTION OF POLYUNSATURATED FATTY ACIDS FROM A CULTURE OF MICROALGAE OF THE PORPHYRIDIUM CRUENTUM

DESCRIPTION.

The invention relates to a process for the selective production of polyunsaturated lipids from a culture of microalgae of the *Porphyridium cruentum* type. Microalgae cultured in a marine medium (NaCl concentration above 0.2M) are often rich in long-chain polyunsaturated fatty acids. These fatty acids have at least 20 carbon atoms and generally more than four unsaturations. They are e.g. arachidonic acid (C 20:4ω6), eicosapentaenoic acid (C 20:5ω3) and docosahexaenoic acid (C 22:6ω3).

These fatty acids have hypocholesterolemic properties and reduce the risks of atherogenesis. These acids are used at present dietetically and are consumed in the form of fish oils. Thus, fish are rich in polyunsaturated lipids, because they accumulate them on consuming plankton microalgae. However, fish oils suffer from two major disadvantages, namely the presence of cholesterol and a strong, unpleasant smell. It would therefore be of interest to replace fish oils directly by oils extracted from microalgae, which do not contain cholesterol and are odourless. Consequently, an attempt has been made to culture microalgae.

Among the microalgae, Rhodophyceae such as *Porphyridium cruentum* contain in majority form three fatty acids, a predominant saturated fatty acid (palmitic acid C 16:0) and two also predominant polyunsaturated fatty acids (arachidonic acid (C 20:4) and eicosapentaenoic acid (C 20:5). Approximately 80% of the C 20:5 occurs in the glycolipids present in the chloroplast membranes, whilst 65% of the C 20:4 occur in the majority phospholipids in the membranes of the cells. Under favourable production conditions, fatty acids represent 2 to 3% of the algal dry matter.

It is known from the article by Tim J. Ahern et al, "Arachidonic Acid Production by the Red Alga *Porphyridium cruentum*", Biotechnology and Bioengineering, Vol. XXV, pp. 1057–1070, 1983 and the article by Zvi Cohen et al., "Effect of Environmental Conditions on Fatty Acid Composition of the Red Alga *Porphyridium cruentum*: Correlation to Growth Rate", J. Phycol, 24, pp. 328–332, 1988, that the content of polyunsaturated fatty acids within these microalgae varies to a marked extent as a function of the culture conditions and in particular the temperature conditions. In the prior art procedures, culturing of the microalgae always takes place in a single stage. However, the optimization of the polyunsaturated fatty acid profile often takes place at a temperature different from that of the optimization of the growth of the microalgae. Consequently, the cultures of microalgae carried out at temperatures above 15° C. give low fatty acid quantities and conversely it is not possible to carry out culturing at a temperature below 15° C., because then there is no growth and no production of biomass.

The problem of the invention is therefore to optimize biomass production, as well as the nature and quantity of lipids rich in polyunsaturated fatty acids.

To this end, the invention relates to a process for the selective production of polyunsaturated lipids from a culture of microalgae of the *Porphyridium cruentum* type.

According to the characteristics of the invention, this process consists of: culturing in a closed tubular photobioreactor the microalga *Porphyridium cruentum*, suspended in a liquid culture medium having a NaCl concentration above 0.2M and a temperature between approximately 20° and 30° C, removing from the photobioreactor at least part of the biomass obtained and placing it in a tank for selective polyunsaturated lipid enrichment, immediately applying to said biomass, for a given period of time, a temperature variation compared with the culturing temperature in the photobioreactor, so as to modify the unsaturation of the fatty acids of the lipids.

Thus, this process makes it possible to optimize the growth of the microalgae by culturing them under optimum conditions and then, separately, during the second stage of the process, obtain a maximum production of polyunsaturated lipids, whilst choosing the nature of the fatty acids contained in said lipids.

According to a first embodiment of the invention, the application of the temperature variation to the biomass consists of bringing the latter to a temperature between approximately 4° and 15° C., so as to obtain lipids more unsaturated than they initially were in the microalgae.

In other words, whereas the microalgae of the *Porphyridium cruentum* type initially contained approximately 57% C 20:4 and 43% C 20:5, after cold treatment, the microalgae contained between 25 and 40% C 20:4 and between 60 and 75% C 20:5.

According to a second embodiment of the invention, the application of the temperature variation to the biomass consists of bringing the latter to a temperature between approximately 30° and 40° C., so as to obtain lipids less unsaturated than they were at the outset in the microalgae.

Advantageously, said temperature variation is applied for at least 12 hours. Thus, after favouring the selection of certain fatty acids, there is also an action on the kinetics of the reaction. Advantageously, into the culture medium is introduced $CO_2$-enriched air with a concentration between approximately 1 and 5%.

Thus, the photosynthesis is assisted and there is an improvement to the culturing conditions of the microalgae within the photobioreactor.

Finally, the production process according to the invention also consists of concentrating the microalgae enriched in polyunsaturated lipids, pulverizing or grinding the microalgae, separating the liquid phase from the solid phase, which contains all the polyunsaturated lipids, extracting said lipids by the addition of a solvent and evaporating said solvent and recovering the polyunsaturated lipids obtained.

The invention is described in greater detail hereinafter relative to a non-limitative embodiment and with reference to the attached drawings, wherein show:

FIG. 1 an overall diagram of a first embodiment of an installation for the selective production of polyunsaturated lipids used for carrying out the process according to the invention.

Figure 2:
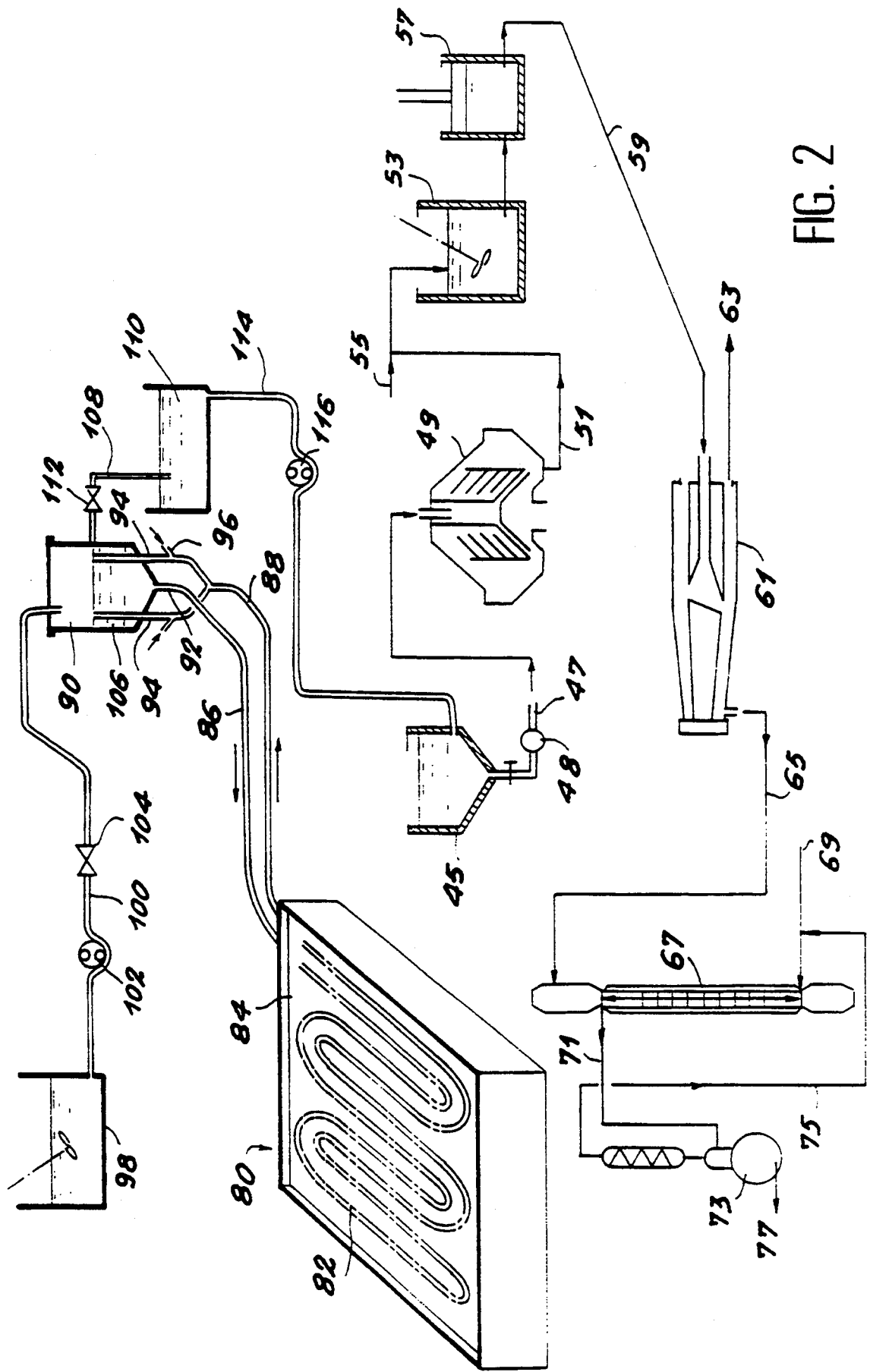

FIG. 2 an overall diagram of a second embodiment of an installation for the selective production of polyunsaturated lipids used for carrying out the process according to the invention.

Figure 3:
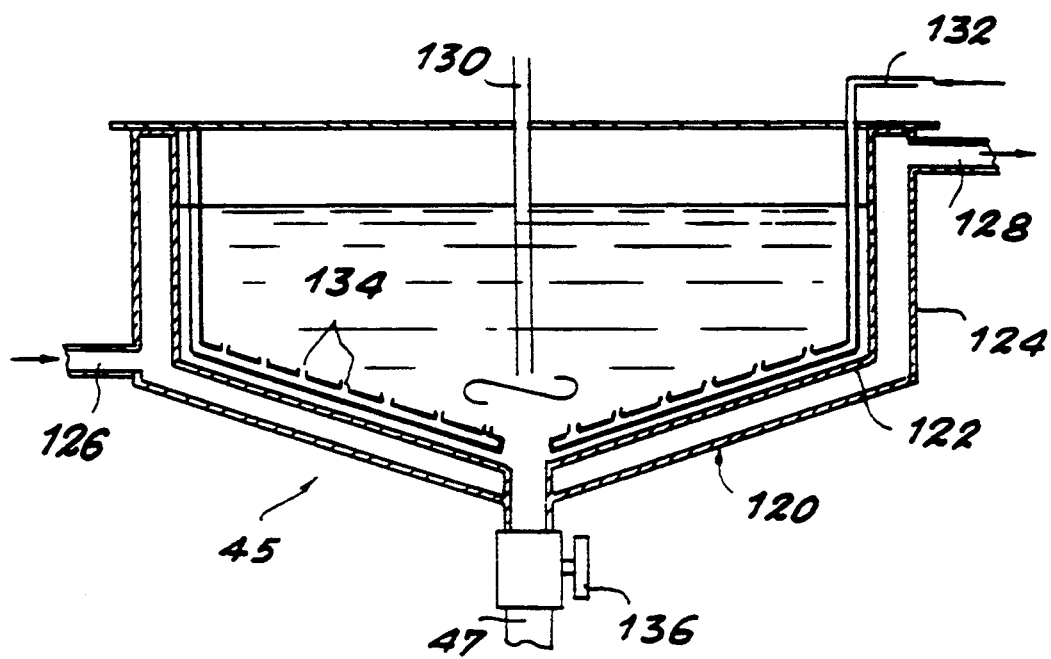

FIG. 3 in more detail one of the elements of FIG. 1, namely an embodiment of the polyunsaturated fatty acid selective enrichment tank.

As illustrated in FIG. 1, the installation making it possible to carry out the process according to the invention, comprises a photobioreactor in which culturing takes place of microalgae of the Porphyridium cruentum type and several apparatuses making it possible to extract said lipids from the biomass obtained.

Culturing of the microalgae takes place in a photobioreactor 1, in the continuous mode ("chemostat"), or ("turbidostat"), so as to obtain a stable biomass quality. Photosynthesis takes place in said photobioreactor.

Photosynthesis is the transformation, as a result of solar energy, of carbon dioxide into hydrocarbon starting material, the oxygen being the main byproduct of said biochemical transformation. This reaction can be symbolized by the following Myers equation:

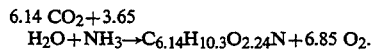

$$6.14\ CO_2 + 3.65\ H_2O + NH_3 \rightarrow C_{6.14}H_{10.3}O_{2.24}N + 6.85\ O_2.$$

The term $C_{6.14}H_{10.3}O_{2.24}N$ corresponds to the biomass.

Nitrogen is supplied in the form of nitrate, urea or ammonium salts introduced into the liquid medium containing the microalgae.

A first embodiment of the photobioreactor permitting an optimum culturing of the microalgae will now be described. The closed photobioreactor 1 has a solar receiver constituted by parallel tubes 3 made from a generally transparent plastics material, such as e.g. polyethylene. Within the said tubes 3 flows the culture medium 5 containing the microalgae and the nutrient elements necessary for their growth.

Advantageously, the culture medium 5 is constituted by artificial sea water of the Hemerick medium type, which has a NaCl concentration higher than 0.2M. This sea water is enriched with oligoelements such as phosphate, potassium or nitrogen. Its pH is between approximately 6 and 8. Its temperature is between 20° and 30° C. The average illumination is 500 to 2000 kcal./m²/d.

Polypropylene collectors 7 and 9 make it possible to interconnect the tubes 3 and ensure the passage of the culture medium 5 between the individual tubes.

A pump 11 connected on a duct 13 links the inlet and the outlet of the photobioreactor 1. This pump ensures the continuous circulation of the culture medium 5. In the embodiment of FIG. 1, the photobioreactor operates continuously. However, it would also be possible to have a second embodiment with a discontinuous or batch operation.

The nutrient medium containing the nutrient elements is prepared, accompanied by stirring, in a tank 15 and is then introduced at the top of a carbonator 17 by a supply duct 19 equipped with a pump 21, which regulates the nutrient medium flow. The $CO_2$ gas is injected under pressure from a reservoir 23 located at the intake of a plunging tube 25 located within the carbonator. This tube 25 permits a $CO_2$ supply in countercurrent to the nutrient medium arriving in the duct 19. The carbonated nutrient medium is injected into the photobioreactor by a supply duct 27 equipped with a pump 29. Thus, the culture medium receives $CO_2$-enriched air at a concentration between approximately 1 and 5%.

For further details on the construction and operation of this solar cell (continuously or discontinuously), reference can be made to FR-A-2,621,323.

The photosynthesis which takes place within the photobioreactor 1 leads to a dissolved oxygen enrichment of the culture, which aids the production of antioxidants of the tocopherol type. On leaving the photobioreactor 1, a duct 41 equipped with a pump 43 brings about the continuous passage of the biomass obtained to a polyunsaturated fatty acid enrichment tank 45. Within the latter, the biomass is subject to a temperature variation. A more detailed description of the structure of said tank and its operation will be given hereinafter.

The polyunsaturated lipid-enriched biomass is sampled from the tank 45 by means of a duct 47, where it is passed by a pump 48 to a centrifuge 49. The centrifuge carries out a concentration stage, where the cellular substances are separated from the culture medium. This concentration stage can also be carried out by filtration or sedimentation.

The centrifuging paste is then passed by a duct 51 to a homogenizing tank 53 equipped with stirring means making it possible to obtain a homogeneous microalgal suspension. It is supplied with buffered medium, i.e. water, plus a phosphate buffer at pH 7.8 by a duct 55. The microalgal suspension is then introduced into a homogenizer-grinder 57, which operates by an alternating sequence of pressure increases and decreases between 300 and 700, namely $1100 \cdot 10^5$ Pa. The temperature is controlled in such a way as to remain below 30° C., so as to cause no deterioration of the lipids. This stage makes it possible to burst the microalgae, so as to separate the solid-liquid fractions from the cellular content.

The crushed or pulverized microalgal suspension is then carried by a duct 59 to a decanter 61 making it possible to separate the microalgal fragments from the buffered medium. This operation could also be carried out by centrifuging. Thus, this stage makes it possible to separate the liquid phase from the solid phase, which contains all the polyunsaturated lipids. The liquid phase is extracted at 63 and contains the buffered medium containing, inter alia, antioxidants such as vitamin C and superoxide dimutase, as well as pigments such as phycobiliproteins. The solid phase is passed by a duct 65 to an extraction column 67 operating in countercurrent manner.

The crushed microalgal residue is introduced by the top part of said extraction column 67, whilst a solvent is introduced at the bottom at 69. The solvent is preferably an organic solvent e.g. chosen from among hexane or chloroform. This polyunsaturated fatty acid-enriched solvent passes out of the upper part of the column at 71 and is passed to the base of an evaporator 73 operating at approximately 40° to 50° C. The solvent passing out of the evaporator 73 by a duct 75 is recycled to the base of the extraction column 67.

At the evaporator outlet 77 is obtained an oil enriched with polyunsaturated fatty acids, antioxidants such as tocopherols ($\alpha, \beta, \gamma$) and carotenoids (more particularly $\beta$-carotene). The presence of antioxidants in the lipid extract containing the fatty acids makes it possible to protect the latter against oxidation phenomena. The antioxidant content is a function of the oxygen content present in the photobioreactor culture medium (cf. also FR-A-2,656,874).

A second embodiment of the photobioreactor will now be described relative to FIG. 2 and is preferable to the first embodiment.

The photobioreactor 80 comprises a plurality of transparent tubes 82, generally made from a rigid plastics material such as Plexiglass (registered trademark). These tubes are interconnected so as to form a coil and are placed on an expanse of thermostatically controlled water 84. This photobioreactor 80 has an inlet tube 86 and an outlet tube 88.

The photobioreactor 80 is connected to a reservoir 90 at a higher level than the photobioreactor. The reservoir 30 is connected to the photobioreactor 80 by a descending tube 92 connected to the inlet tube 86 and by two ascending tubes 94 connected to the outlet tube 88. An injector 96 is placed at the base of each ascending tube 94 and permits the simultaneous injection of a gas constituted by air and $CO_2$.

The nutrient medium containing the nutrient elements is prepared, accompanied by stirring, in a tank 98 and is then introduced at the top of the reservoir 90 by a supply duct 100. A peristaltic pump 102 and a valve 104 are present on said supply duct 100.

The culture medium 106 (containing the microalgae and the nutrient medium) is contained in the reservoir 90, flowing by gravity to the photobioreactor 80 through the descending tube 92. After circulating in the photobioreactor 80, the culture medium reaches the outlet tube 88. The medium is then raised again into the reservoir as a result of an adequate injection of gas by the injector 96, which has the effect of reducing the density of the liquid medium. The injected gas not only makes it possible to circulate the culture medium within the photobioreactor 80, but also enables the addition of the $CO_2$ necessary for photosynthesis.

A duct 108 forming an overflow makes it possible to continuously discharge the culture medium from the reservoir 90 in the direction of an intermediate storage tank 110. The duct 108 has a valve 112. The intermediate storage tank 110 is connected to the enrichment tank 45 by a duct 114 on which is provided a peristaltic pump 116. The pump 116 makes it possible to supply the culture medium to the enrichment tank 45 at a given flow rate, which can differ from the discharge flow rate from the reservoir 90, hence the need for the intermediate storage tank 110.

The remainder of the extraction apparatus is identical to that described in connection with the first embodiment according to FIG. 1.

The structure of the enrichment tank 45 will now be described in greater detail with particular reference to FIG. 3. The tank 45 is preferably cylindrical and is provided with a conical base 120. It is formed by a double wall (inner wall 122 and outer wall 124). This tank is also provided with an inlet 126 and an outlet 128 permitting the circulation between the two walls 122, 124 of a cooling or heating liquid, so as to bring about the thermal shock.

The form of this tank is particularly well suited to bringing about a good thermal regulation and a good fluid flow. Moreover, the tank is thermostatically controlled so as to maintain the selected hot or cold temperature.

The tank 45 also has a stirring device 130 making it possible to stir the biomass and aid its contact with the inner wall 122, where the heat exchanges takes place. The tank 45 also comprises an air injection device 132 constituted by a duct extending within the tank 45 along the inner wall 122 and provided in the bottom of the tank (conical part) with air outlet orifices 134. This air injecting device 132 prevents adhesion of microalgae to the walls and the possible introduction of $CO_2$ mixed with air.

This tank has a valve 136 located on the discharge duct 47. The valve 136 makes it possible to remove the culture in order to carry out the subsequent extraction stages of the process. The biomass can be placed at time zero in the tank 45 and removed in its entirety at the end of a given period (batch or discontinuous operation) or can be replenished and permanently removed (continuous operation). In the second case, the culture is continuously supplied to the tank 45 via a pump, whose delivery will be chosen as a function of the desired residence time in the tank, the culture being continuously removed by an overflow. Neither the pump, nor the overflow are shown in FIG. 2.

Finally, said tank is generally placed under a light intensity between 20 and 300 $\mu E/m^2/s$.

The particular form of the tank 45 described hereinbefore only constitutes one embodiment. It would also be possible to have a tank with a different form without passing outside the scope of the invention.

It has also been demonstrated that the preferred selection of C 20:4 and C 20:5 depended on the dilution rate, i.e. the reverse of the residence time of the microalgae in the photobioreactor 1 or 80.

This dilution rate is generally between 1 and 0.1 $d^{-1}$ as a function of the light intensity received by the microalgae, their photo-period, the temperature, the climatic conditions or the fatty acid aimed at. Microalgae cultured with a high dilution rate of between approximately 0.3 and 1 $d^{-1}$ (short residence time in the photobioreactor) contained more C 20:5 and conversely those cultured with a low dilution rate e.g. between 0.1 and 0.3 $d^{-1}$ (long residence time in the photobioreactor) contained more C 20:4. However, these values are only given for information purposes.

It should also be noted that biomass production increases when the dilution rate increases.

It has been found that as a function of the extent of the temperature variation applied and the application time thereof, there was a modification to the biomass content of C 20:4 or C 20:5 and the ratio R between C 20:5 and C 20:4. In order to mainly obtain C 20:5 (ratio R above 1), a "cold" temperature variation was carried out, i.e. the biomass was treated at a temperature below 15° C. and preferably between 4° and 15° C. However, if it was wished to obtain a higher C 20:4 concentration (ratio R below 1), a "hot" temperature variation was carried out, i.e. at a temperature above 30° C. and preferably between 30° and 40° C.

The application time of said temperature variation is a function of the desired C 20:5 or C 20:4 content, but generally varies between 12 hours and 5 days (120 hours).

In general, there will be a combination of the dilution rates and the directions of the temperature variations so as to vary the ratio R in one or other directions.

Four examples of cultures produced will now be described.

EXAMPLE 1

The microalga *Porphyridium cruentum* was cultured in a closed photobioreactor, in the continuous mode, at a temperature between 22° and 25° C.

The dilution rate corresponding to the inverse of the residence time in the photobioreactor was 0.15 $d^{-1}$. In other words, these microalgae were cultured for approximately 6 days in the photobioreactor giving a biomass productivity of 10 g/m²/d. The distribution of majority fatty acids was as follows:

C 16:0=30.8% total fatty acids (TFA)
C 20:4=23.4% TFA,
C 20:5=16.8% TFA.

$$\text{The ratio } R = \frac{C\ 20:5}{C\ 20:4} = 0.72$$

EXAMPLE 2

Microalgae of *Porphyridium cruentum* were cultured in a closed photobioreactor, in the continuous mode, at a temperature of 26° C. and under a strong light intensity.

Variations were made to the dilution rate and the majority fatty acid distribution in the following way:

dilution rate=0.5 d$^{-1}$,
C 20:4=4% total fatty acids (TFA),
C 20:5=15% TFA
ratio R=3.75, dilution rate=0.16 d$^{-1}$,
C 20:4=6% TFA,
C 20:5=8% TFA,
ratio R=1.33.

This shows that the C 20:5 quantity increases when the dilution rate increases.

EXAMPLE 3

Microalgae of *Porphyridium cruentum* were cultured in a closed photobioreactor, in the continuous mode, at a temperature of 22° C. and at a dilution rate of 0.3 d$^{-1}$. This was followed by the application of a temperature variation bringing the biomass to a temperature of 12° C., under a light intensity of 30 μE/m²/s and without CO$_2$ enrichment.

As a function of the residence time of the culture at 12° C. (duration of the temperature variation) the following majority fatty acid distributions were observed.

Initial distribution (culture from photobioreactor 1):

C 16:0=31.4% total fatty acids (TFA),
C 20:4=27.1% TFA,
C 20:5=19.8% TFA, and
R=0.73,
Residence time=52 hours.

C 16:0=26.9% TFA,
C 20:4=21.9% TFA,
C 20:5=30.6% TFA,
R=1.40,
Residence time=97 hours.

C 16:0=28.3% TFA,
C 20:4=16.5% TFA,
C 20:5=33.4% TFA,
R=2.02,
Residence time=144 hours.

C 16:0=27.5% TFA,
C 20:4=14.5% TFA,
C 20:5=38.1% TFA,
R=2.63.

On comparing Examples 1 and 2 before making the temperature variation, it can be seen that despite a slightly different dilution rate, the ratio R is similar, whereas with a higher dilution rate (Example 2), the percentage of polyunsaturated fatty acids compared with the total fatty acids is increased.

A cold temperature variation leads to an increase in the C 20:5 content (and therefore to an increase of R). Thus, when the microalga is subject to such a temperature variation, it reacts so as to maintain a certain membrane fluidity compatible with photosynthesis and membrane exchanges.

EXAMPLE 4

Microalgae of type *Porphyridium cruentum* were cultured at a temperature of 22° C. and a dilution rate of 0.3 d$^{-1}$ in a closed tubular photobioreactor. This was followed by the application of a thermal shock bringing the biomass to a temperature of 12° C. for 144 h. The culture was then concentrated by centrifuging to a dry matter content of 20 g/l. This culture was pulverized in a homogenizer at a pressure of 500·10⁵ Pa under thermal control, followed by the centrifuging or filtering thereof.

The polyunsaturated lipids were extracted from the solid phase by a chloroform:methanol:water mixture (2:2:1.8). The thus extracted lipid fraction represents 11.5% of the algal dry matter. This fraction contains 36% total fatty acids. Among these fatty acids, the C 20:4 represent 14.5% thereof and C 20:5 38.1% thereof. The thus obtained oil, coloured by carotenoids, therefore contains in all 5.2% C 20:4 and 13.7% 20:5 (R=2.63).

We claim:
1. A process for the selective production of polyunsaturated fatty acids from a culture of microalgae of *Porphyridium cruentum* comprising:
   i) culturing *Porphyridium cruentum* suspended in a liquid culture medium, in a closed, tubular photobioreactor, wherein said culture medium is adapted for the culture of *Porphyridium cruentum*, having an NaCl concentration above 0.2M, at a temperature of between approximately 20 and 30 degrees Celsius to form a biomass;
   ii) removing from said photobioreactor at least a part of said biomass;
   iii) cooling the removed biomass to a temperature of between approximately 4° and 15° C. for a period of at least 12 hours, thereby effecting an increase of the ratio of C 20:5 to C 20:4 unsaturated fatty acids in said removed biomass as compared to the ratio prior to the application of cooling.
2. The process of claim 1, further comprising after step (iii);
   iv) concentrating the removed biomass;
   v) pulverizing the microalgae therein;
   vi) separating a liquid phase from a solid phase, solid phase containing said polyunsaturated fatty acids;
   vii) extracting said polyunsaturated fatty acids using an organic solvent; and
   viii) evaporating said organic solvent to obtain said polyunsaturated fatty acids.
3. The process of claim 1, wherein said cooling period is between 12 and 120 hours.
4. The process of claim 1, wherein the residence time of the *Porphyrium cruentum* in the photobioreactor is between 1 and 10 days.

5. The process of claim 1, wherein $CO_2$-enriched air, at a concentration of between approximately 1 and 5% is introduced into said culture medium.

6. The process of claim 1, wherein a pH of said culture medium in said photobioreactor is between approximately 6 and 8.

7. The process of claim 1, wherein an average illumination of between 500–2,000 $kcal/m^2/d$ is applied within said photobioreactor.

8. The process of claim 2, wherein said microalgae are pulverized in a homogenizer pulverizer at a temperature below approximately 30° C. and at a pressure exceeding $300 \times 10^5$ Pa.

9. The process of claim 2, wherein said organic solvent is selected from the group consisting of chloroform and hexane.

* * * * *